Figure 1:
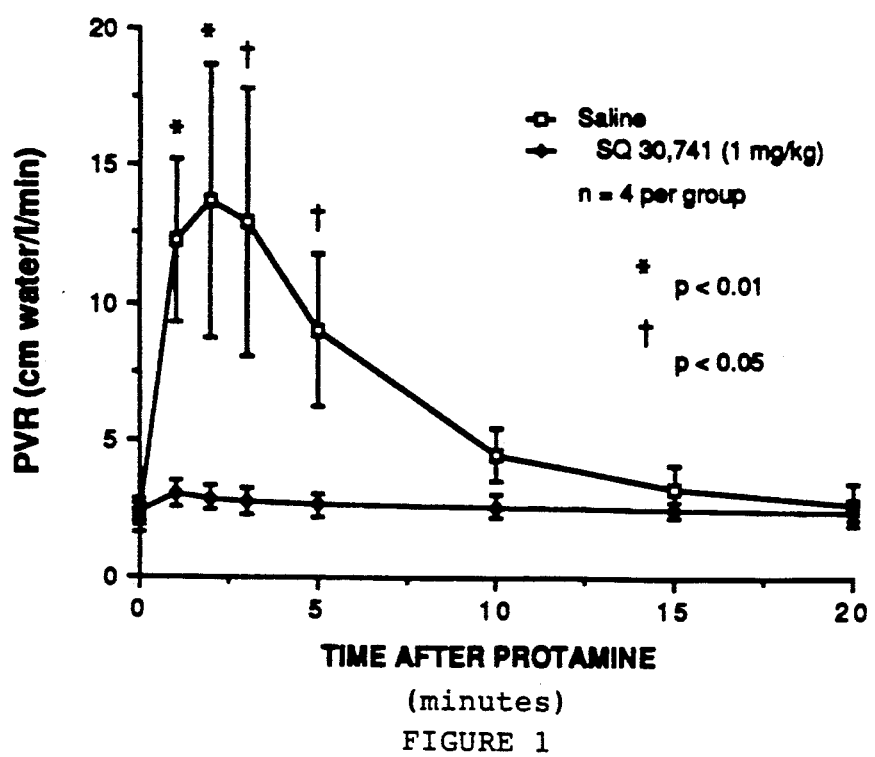

United States Patent [19]

Ogletree et al.

[11] Patent Number: 5,066,480

[45] Date of Patent: Nov. 19, 1991

[54] METHOD OF PREVENTING OR REDUCING ADVERSE REACTIONS TO PROTAMINE USING A THROMBOXANE $A_2$ RECEPTOR ANTAGONIST

[75] Inventors: Martin L. Ogletree; William A. Schumacher, both of Newtown, Pa.; Gary J. Grover, Stockton, N.J.; Lawrence T. Friedhoff, Philadelphia, Pa.

[73] Assignee: E. R. Squibb & Sons, Inc., Princeton, N.J.

[21] Appl. No.: 179,694

[22] Filed: Apr. 11, 1988

[51] Int. Cl.[5] ............................................. A61K 49/00
[52] U.S. Cl. ..................................... 424/10; 514/823; 514/922
[58] Field of Search .................... 424/10; 514/922, 823

[56] References Cited

U.S. PATENT DOCUMENTS

| | | | |
|---|---|---|---|
| 4,258,058 | 3/1981 | Witte et al. | 514/562 |
| 4,416,896 | 11/1983 | Nakane et al. | 514/469 |
| 4,443,477 | 4/1984 | Witte et al. | 514/562 |
| 4,663,336 | 5/1987 | Nakane et al. | 514/469 |

OTHER PUBLICATIONS

Morel et al., Chem. Abst. 107(5): 37778p (1987).
The Merck Manual, pp. 2514–2515, (1987).
Degges et al., "Pulmonary Hypertensive Effect of Heparin and Protamine Interaction; Evidence for Thromboxane $B_2$ Release from Lung", Am. Jour. Surg., vol. 154, pp. 696–699, Dec. 1987.
Schumacher et al., "Effect of the Thromboxane $A_2$ Receptor Antagonist, SQ 29,548 and SQ 28,668, on the Pulmonary Hypertensive Response to Endotoxemia in Swine", Pharm. 34: 301–308 (1987).

Primary Examiner—Glennon H. Hollrah
Assistant Examiner—Gary E. Hollinden
Attorney, Agent, or Firm—Burton Rodney

[57] ABSTRACT

A method is provided for preventing reducing or reversing adverse reactions, such as pulmonary hypertension produced when protamine interacts with heparin, by administering a thromboxane $A_2$ receptor antagonist.

20 Claims, 3 Drawing Sheets

METHOD OF PREVENTING OR REDUCING ADVERSE REACTIONS TO PROTAMINE USING A THROMBOXANE A₂ RECEPTOR ANTAGONIST

FIELD OF THE INVENTION

The present invention relates to a method for preventing, reversing or reducing adverse reactions, such as pulmonary hypertension produced when protamine interacts with the anticoagulant heparin, by administering a thromboxane $A_2$ receptor antagonist.

BACKGROUND OF THE INVENTION

Thromboxane $A_2$ receptor antagonists have been found to be effective in preventing early pulmonary hypertension induced by exposure to endotoxin, Schumacher, W. A. et al., "Effect of the $TxA_2$-receptor antagonists SQ 29,548 and SQ 28,688 on the pulmonary hypertensive response to endotoxemia in swine," Pharmacology 34:301–308, 1987.

Protamines are simple proteins of low molecular weight that are rich in basic amino acids. Protamine is a cationic protein which is used in man to reverse the anticoagulant activity of heparin. It reacts with anionic heparin to form a complex which is inactive as an anticoagulant.

Upon completion of surgical procedures requiring anticoagulant treatment, it is desirable to restore normal function to the blood coagulation cascade to minimize post-operative bleeding. When heparin is employed as the anticoagulant, protamine is often infused to neutralize the heparin-induced anticoagulant activity. Thus, protamine acts as a heparin antagonist and is used to neutralize heparin in surgical procedures.

Unfortunately, certain patients show intolerance to protamine. Adverse reactions which may result from the interaction between protamine and heparin include anaphylaxis and pulmonary hypertension. The latter response, when produced in pigs, can be significantly blunted by pretreatment with aspirin and is associated with enhanced $TxB_2$ blood levels, Degges, R. D. et al., "Pulmonary hypertensive effect of heparin and protamine interaction; evidence for thromboxane $B_2$ release from the lung," Am. J. Surg. 154:696–698, 1987. The Physicians' Desk Reference, 41st Edition, 1987, pp. 1162–1163, indicates that "Because fatal reactions often resembling anaphylaxis have been reported after administration of protamine sulfate, the drug should be given only when resuscitation techniques and treatment of anaphylactoid shock are readily available."

DESCRIPTION OF THE INVENTION

In accordance with the present invention, a method is provided for preventing, reducing or reversing adverse side effects caused by protamine-induced neutralization of heparin in mammalian species, such as protamine/heparin induced pulmonary hypertension, wherein a therapeutically effective amount of a thromboxane $A_2$ receptor antagonist is systemically administered, such as orally, parenterally, transdermally, or by inhalation to prevent, reverse or mitigate adverse effects of protamine.

The term "thromboxane $A_2$ receptor antagonist" as employed herein includes compounds which are so-called thromboxane $A_2$ receptor antagonists, thromboxane $A_2$ antagonists, thromboxane $A_2$/prostaglandin endoperoxide antagonists, TP-receptor antagonists, or thromboxane antagonists except insofar as the compound is an inhibitor of thromboxane synthesis but not an antagonist of thromboxane $A_2$ receptor mediated responses.

Thromboxane $A_2$ receptor antagonists which may be employed herein include the 7-oxabicycloheptane and 7-oxabicycloheptene compounds disclosed in U.S. Pat. No. 4,537,981 to Snitman et al, especially, [1S-[1α,2β(5Z),3β(1E, 3R, 4S),4α]]-7-[3-(3-hydroxy-4-phenyl-1-pentenyl)-7-oxabicyclo-[2.2.1]hept-2-yl]-5-heptenoic acid; the 7-oxabicycloheptane substituted aminoprostaglandin analogs disclosed in U.S. Pat. No. 4,416,896 to Nakane et al., especially, [1S-[1α,2β(5Z),3β,4α]]-7-[3-[[2-(phenylamino)carbonyl]hydrazino]methyl]-7-oxabicyclo[2.2.1]hept-2-yl]-5-heptenoic acid; the 7-oxabicycloheptane substituted diamide prostaglandin analogs disclosed in U.S. Pat. No. 4,663,336 to Nakane et al, especially, [1S-[1β,2α(5Z),3α,5β]]-7-[3-[[[[(1-oxoheptyl)-amino]acetyl]amino]methyl]-7-oxabicyclo[2.2.1]- hept-2-yl]-5-heptenoic acid and the corresponding tetrazole, and [1S-[1<α,2<β(Z),3<β,4<α[[-7-[3-[[[[(4-cyclohexyl-1-oxobutyl)amino]acetyl]amino]methyl]-7-oxabicyclo[2.2.1hept-2-yl]-5-heptenoic acid; the phenoxyalkyl carboxylic acids disclosed in U.S. Pat. No. 4,258,058 to Witte et al, especially 4-[2-(benzenesulfamido)ethyl]phenoxyacetic acid, (BM 13,177 - Boehringer Mannheim), the sulphonamidophenyl carboxylic acids disclosed in U.S. Pat. No. 4,443,477 to Witte et al, especially 4-[2-(4-chlorobenzenesulfonamido)-ethyl]phenylacetic acid, (BM 13,505, Boehringer Mannheim) the arylthioalkylphenyl carboxylic acids disclosed in U.S. application Ser. No. 067,199 filed June 29, 1987, especially 4-(3-((4-chlorophenyl) sulfonyl)propyl)benzeneacetic acid.

Other examples of thromboxane $A_2$ receptor antagonists suitable for use herein include, but are not limited to (E)-5-[[[(pyridinyl)[3-(trifluoromethyl) phenyl]methylene]amino]oxy]pentanoic acid also referred to as R68,070 - Janssen Research Laboratories, 3-[1-(4-chlorophenylmethyl)-5-fluoro-3-methylindol-2-yl]-2,2-dimethylpropanoic acid [(L-655240 Merck-Frosst) Eur. J. Pharmacol. 135(2):193, 17 Mar. 87], 5(Z)-7-([2,4,5-cis]-4-(2-hydroxyphenyl)-2-trifluoromethyl-1,3-dioxan-5-yl)heptenoic acid (ICI 185282, Brit. J. Pharmacol 90 (Proc. Suppl):228 P-Abs., Mar. 87), 5(Z)-7-[2,2-dimethyl-4-phenyl-1,3-dioxan-cis-5-yl]-heptenoic acid (ICI 159995, Brit. J. Pharmacol. 86 (Proc. Suppl):808 P-Abs., Dec. 85), N,N'-bis[7-(3-chlorobenzeneaminosulfonyl)-1,2,3,4- tetrahydro-isoquinolyl]disulfonylimide (SKF 88046, Pharmacologist 25(3):116 Abs, 117 Abs, Aug. 83), [1α(Z)-2β,5α]-(+)-7-[5-[[(1,1'-biphenyl)-4-yl]methoxy]-2-(4-morpholinyl)-3-oxocyclopentyl-4-heptenoic acid (AH 23848 - Glaxo, Circulation 72(6):1208, Dec. 85), GR32191-Glaxo (Thromb. Haemostas, 58 (1) 181 (1987), levallorphan allyl bromide (CM 32,191, Sanofi, Life Sci. 31 (20–21):2261, 15 Nov. 82), (Z,2-endo-3-oxo)-7-(3-acetyl-2-bicyclo[2.2.1]heptyl-5-hepta-3Z-enoic acid, 4-phenylthiosemicarbazone (EP092 - Univ. Edinburgh, Brit, J. Pharmacol. 84(3):595, Mar. 85).

The disclosure of the above-mentioned patents, patent applications and other references are incorporated herein by reference.

In carrying out the method of the present invention, the thromboxane $A_2$ receptor antagonist may be administered systemically, such as orally or parenterally or transdermally, to mammalian species, such as monkeys, dogs, cats, rats, humans. Thus, the thromboxane $A_2$ receptor antagonist may be administered, for example, orally, intravenously, intrapulmonary arterially, intraarterially, transdermally, or by inhalation to provide a dosage of from about 10 μg/kg to about 10 mg/kg and preferably from about 0.1 mg/kg to about 5 mg/kg. The thromboxane antagonist may be administered (1) before administering protamine, (2) with protamine, (3) with heparin or (4) within several minutes after administering protamine.

The thromboxane $A_2$ receptor antagonist may be incorporated in a conventional dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid or sodium bisulfite) or the like. Parenteral dosage forms are preferred, although oral, transdermal, and aerosol forms are quite satisfactory as well.

With regard to such systemic formulations, single or divided doses of from about 0.5 to about 2500 mg, preferably from about 5 to 2000 mg/one to four times daily, may be administered in systemic dosage forms as described above.

The thromboxane $A_2$ receptor antagonist may be administered throughout the period of administering protamine or may be administered to treat the adverse reactions caused by protamine for a period until such conditions are reversed.

Figure 2:
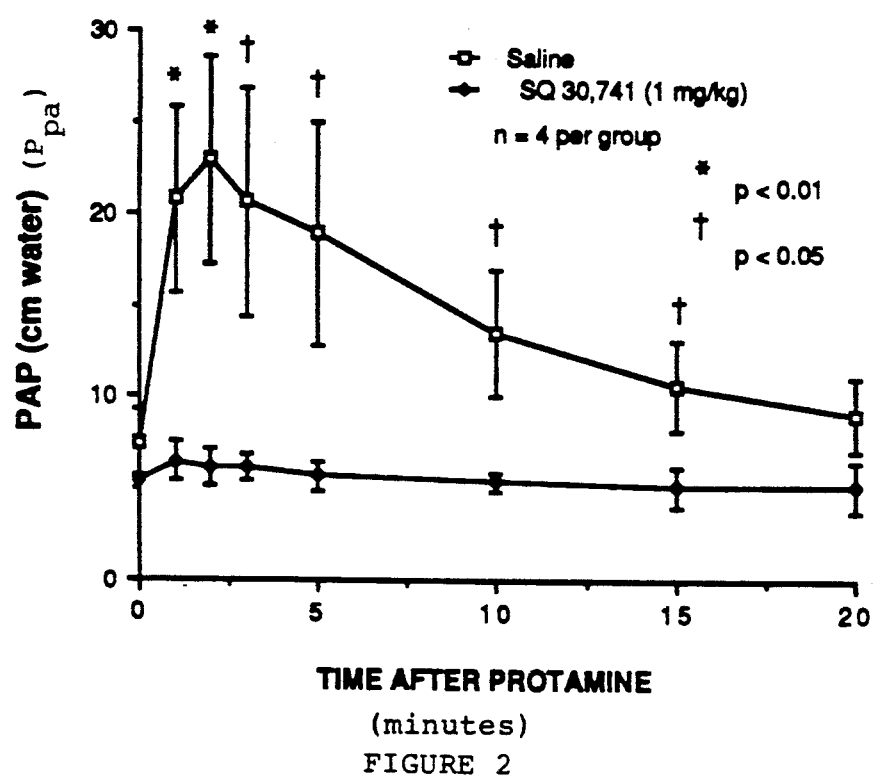
Figure 3:
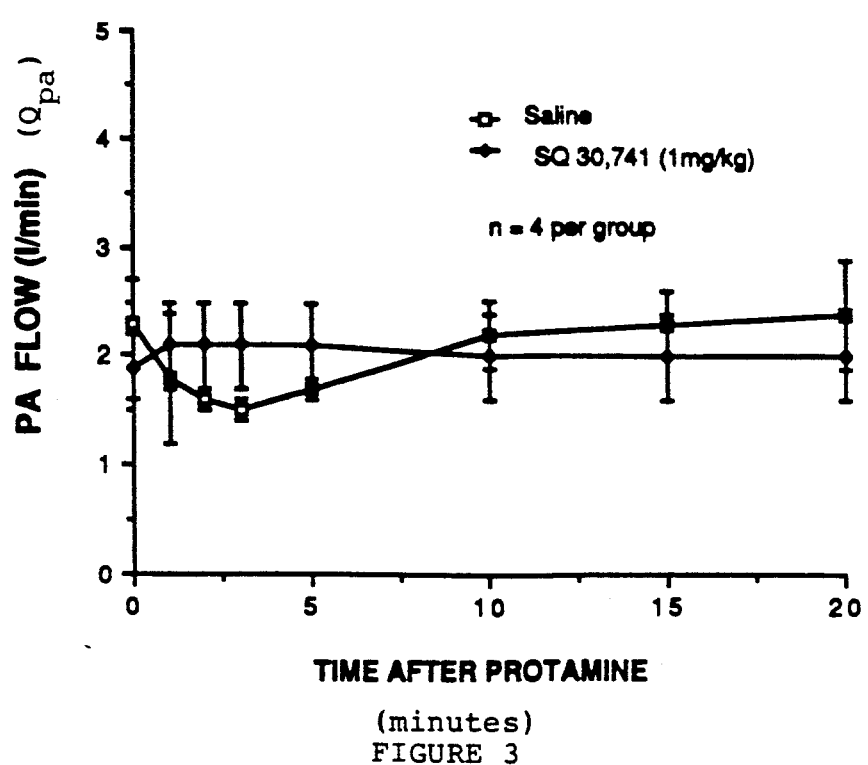

FIGS. 1, 2, and 3 illustrate the effect of the thromboxane $A_2$ receptor antagonist on the pulmonary hypertensive response to protamine reversal of heparin in anesthetized pigs.

The following Examples represent preferred embodiments of the present invention.

EXAMPLE 1

An injectable solution of thromboxane $A_2$ receptor antagonist for intravenous or intraarterial use in preventing or reversing the effects of protamine is produced as follows:

[1S-[1α,2β(5Z),3β,4α]]-7-[3-[[2-(phenylamino)carbonyl]hydrazino-methyl]-7-oxabicyclo[2.2.1]hept-2-yl]-5-heptenoic acid (SQ 29,548):2500 mg
Methyl paraben:5 mg
Propyl paraben:1 mg
Sodium chloride:25 g
Water for injection qs.:5 l.

The thromboxane $A_2$ receptor antagonist, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains a concentration of 75 mg of active ingredient per 150 ml of solution.

EXAMPLE 2

An injectable for use in preventing or reversing the effects of protamine is prepared as described in Example 1 except that the thromboxane $A_2$ receptor antagonist employed is the phenoxyalkyl carboxylic acid 4-[2-(benzenesulfamido)ethyl]phenoxyacetic acid, disclosed in U.S. Pat. No. 4,258,058.

EXAMPLE 3

An injectable solution of thromboxane $A_2$ receptor antagonist for intravenous or intraarterial use containing [1S-[1β,2β(5Z),3α,4β]]-7-[3-[[[[(1-oxoheptyl)amino]acetyl]amino]methyl]-7-oxabicyclo 2.2.1]hept-2-yl]-5-heptenoic acid (SQ 30,741) as the thromboxane $A_2$ receptor antagonist is prepared as described in Example 1.

EXAMPLE 4

An injectable for use in preventing or reversing the effects of protamine is prepared as described in Example 1 except that the thromboxane $A_2$ receptor antagonist employed is [1S-[1<α,2<β(Z),- 3<β,4<α]]-7-[3-[[[[(4-cyclohexyl-1-oxobutyl)amino]-acetyl]amino]methyl]-7-oxabicyclo[2.2.1]hept-2-yl]-5-heptenoic acid.

EXAMPLE 5

A thromboxane $A_2$ antagonist formulation suitable for oral administration is set out below.

1000 tablets each containing 400 mg of thromboxane $A_2$ receptor antagonist are produced from the following ingredients. [1S-[1α,2α(5Z),3α,4β]]-7-[3-[[[[(1-Oxoheptyl)amino]acetyl]amino]methyl]-7-oxabicyclo[2.2.1-]hept-2-yl]-5-heptenoic acid (SQ 30,741):400 g
Corn starch:50 g
Gelatin:7.5 g
Avicel (microcrystalline cellulose):25 g
Magnesium stearate:2.5 g The thromboxane $A_2$ receptor antagonist and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 400 mg of active ingredient.

EXAMPLES 6 and 7

The following aerosol (inhalation) formulations may be used in preventing or reversing the effects of protamine and may be administered by itself or in conjunction with an inhalation anesthetic.

| Example 6 | | Amount % by Wt. | Specific Amount % by Wt. |
|---|---|---|---|
| SQ 30,471 | | 0.01 to 1 | 0.05 |
| Ethanol | | 5–50 | 25 |
| Freon 11 or 114 | 50-50 | | |
| Freon 12 | mixture | 50–95 | 74.95 |

| Example 7 | | % by Wt. |
|---|---|---|
| SQ 30,741 | | 0.01–1 |
| Surfactant (Oleic acid, oleyl alcohol, lecithin) | | qs. |
| Water | | qs. |
| Freon 11 or 114 | 50-50 | |
| Freon 12 | mixture | qs. to 100% |

EXAMPLE 8

The effect of the thromboxane $A_2$ receptor antagonist SQ 30,741 on the pulmonary hypertensive response produced by the interaction of protamine with heparin was determined in pentobarbitalanesthetized pigs.

Yucatan minipigs (Charles Rivers, Willmington, MA) of either sex weighing 24 to 25 kg were anesthetized with Na-pentabarbital (~40 mg/kg, i.p.) and supplemented as required i.v. A jugular vein and carotid artery were cannulated with PE205 tubing and the arterial catheter attached to a Model P23D pressure transducer (Gould Inc., Oxnard, CA). The trachea was cannulated and the animal ventilated with a Model 613 respirator (Harvard Apparatus, Natick, MA). The heart was isolated by a left thoracotomy and suspended in a pericardial cradle. An EP435 or EP440 electromagnetic flow probe (Carolina Medical Electronics, Inc., King, NC) was attached to the pulmonary artery. A Model SPC350 5-French catheter pressure transducer (Millar Instruments Inc., Houston, TX) and an infusion cannula, constructed from a 22 gauge hypodermic needle tip attached to PE50 tubing, were inserted into the pulmonary artery proximal to the flow probe. Another catheter pressure transducer was inserted into the tip of the left atrium and placed at the same level as the pulmonary artery pressure transducer. Continuous recordings were made of arterial blood pressure (ABP), pulmonary artery pressure) ($P_{pa}$) (FIG. 2), left atrial pressure ($P_{la}$) and pulmonary artery flow ($Q_{pa}$) (FIG. 3) on a Model 7 recorder (Grass Instrument Co., Quincy, MA). Pulmonary vascular resistance (PVR) (FIG. 1) was calculated from the ratio of $(P_{pa}-P_{la})/q_{PA}$.

A period of 30 minutes was allowed for equilibration, during which time blood gases were analyzed and respiration adjusted to obtain a $PCO_2$ of 30 to 35 mm Hg and a $PO_2$ of 80 to 100 mm Hg. Heparin of porcine intestinal mucosal origin (300 U/kg, i.v.; #H-3125, Sigma Chemical Co., St. Louis, MO) was administered 15 minutes before protamine (3 mg/kg; Lyphomed, Rosemont, IL). The protamine was injected into the pulmonary artery over a 15 second interval. SQ 30,741 (1 mg/kg) or Vehicle (1.5 ml saline) was also delivered directly into the pulmonary artery at 2 minutes before protamine. Physiological parameters were determined immediately before (0 minute) and at 2, 5, 10 and 20 minutes after protamine.

Data were analyzed using a microcomputer statistics package (Systat, Evanston, IL). An analysis of variance employing repeated measures with grouping factors was used for between treatment comparisons, and a one-way repeated measures design was used for within group comparisons. All data in the text and Figures are expressed as mean $\pm SE$.

Control values for pulmonary artery pressure ($P_{pa}$), pulmonary artery flow ($Q_{pa}$) and pulmonary vascular resistance (PVR) did not differ between the SQ 30,741 and saline groups. Following administration of protamine, $P_{pa}$ and PVR were significantly increased with saline treatment (FIGS. 2 and 1, respectively). The pulmonary hypertension observed in saline-treated animals was maximal within 2 to 3 minutes and quickly subsided. The major factor accounting for the $808\pm183\%$ ($p<0.05$) increase in PVR was a $230\pm26\%$ ($p<0.05$) increase in ($P_{pa}$) without any change in $P_{la}$ ($-10\pm17\%$, NS). There was a tendency for $Q_{pa}$ to decrease (FIG. 3), but this did not attain statistical significance ($-40\pm13\%$, $p=0.11$), probably attributable to the small number of animals. No changes were detected in SQ 30,741 treated animals in either PVR ($14\pm11\%$, NS), $P_{pa}$ ($19\pm12\%$, NS) or $Q_{pa}$ ($4\pm2\%$, NS).

The pulmonary hypertensive response associated with protamine administration following heparin was qualitatively similar to that observed in conscious pigs by Fischer, W. P., Fewell, J.E., Hill, D. E., Barnes, R. W. and Read, R. C., "Cardiovascular effects of protamine sulfate are dependent on the presence and type of circulating heparin," J. Thorac. Cardiovasc. Surg. 89:63-70, 1985. They observed that protamine alone did not evoke the response and that porcine mucosal heparin was more provocative than heparin obtained from beef lung. The same doses of heparin and protamine were used in this experiment as reported by Fischer et al, with the amount of protamine exceeding by 15% that calculated to totally reverse heparin activity.

The ability of SQ 30,741 to prevent the increase in PVR produced by the protamine-heparin interaction demonstrates that $TxA_2$-receptor stimulation is essential for the response. Although a small number of animals were studied, highly significant ($p<0.01$) differences were detected between SQ 30,741 and saline treatments. Almost total (94%) blockade of the $P_{pa}$ increase in response to the same stimulus was also reported with aspirin (Degges et al, 1987). However, the irreversibility of the cyclooxygenase inhibitor would be a disadvantage in many post-operative clinical settings in which protamine is used. Overall, these data suggest that SQ 30,741 would be a useful agent in reducing the acute toxicity of protamine in its use to reverse heparin-induced anticoagulation.

In view of the above, it appears that $TxA_2$ receptor antagonists would be useful in reducing the potential toxic effects associated with protamine administration in clinical settings.

What is claimed is:

1. A method for treating pulmonary hypertension caused by protamine induced neutralization of heparin, in a mammalian species, which comprises administering to a mammalian species in need of such treatment an effective amount of a thromboxane $A_2$ receptor antagonist which acts only on thromboxane $A_2$receptors.

2. The method as defined in claim 1 wherein the thromboxane $A_2$ receptor antagonist is administered systemically.

3. The method as defined in claim 1 wherein the thromboxane $A_2$ receptor antagonist is administered intravenously, orally, intraarterially, intrapulmonary arterially, transdermally, or by inhalation.

4. The method as defined in claim 1 wherein the thromboxane $A_2$ receptor antagonist is administered after administration of protamine.

5. The method as defined in claim 1 wherein the thromboxane $A_2$ receptor antagonist is administered prior to administration of protamine.

6. The method as defined in claim 1 wherein the thromboxane $A_2$ receptor antagonist is a 7-oxabicycloheptane or a 7-oxabicycloheptene.

7. The method as defined in claim 1 wherein the thromboxane $A_2$ receptor antagonist is a 7-oxabicycloheptane substituted amino-prostaglandin analog.

8. The method as defined in claim 1 wherein the thromboxane $A_2$ receptor antagonist is a 7-oxabicycloheptane substituted diamide prostaglandin analog.

9. The method as defined in claim 1 wherein the thromboxane $A_2$ receptor antagonist is a phenoxyalkyl carboxylic acid.

10. The method as defined in claim 1 wherein the thromboxane $A_2$ receptor antagonist is a sulfonamidophenyl carboxylic acid.

11. The method as defined in claim 1 wherein the thromboxane $A_2$ receptor antagonist is an arylthioalkylphenyl carboxylic acid.

12. The method as defined in claim 1 wherein the thromboxane $A_2$ receptor antagonist is [1S-

[1α,2β(5Z),3β(1E,3R,4S),4α]]-7-[3-(3-hydroxy-4-phenyl-1-pentenyl)-7-oxabicyclo-2.2.1]hept-2-yl]-5-heptenoic acid.

13. The method as defined in claim 1 wherein the thromboxane A₂ receptor antagonist has the name [1S-[1β,2α(5Z),3α,4β]]-7-[3-[[[[(1-oxoheptyl)amino]acetyl]amino]methyl]-7-oxabicyclo-2.2.1]hept-2-yl]-5-heptenoic acid or the corresponding tetrazole.

14. The method as defined in claim 1 wherein the thromboxane A₂ receptor antagonist has the name [1S-[1<α,2β(Z),3<β,4<α]]-7-[3-[[[[(4-cyclohexyl-1-oxobutyl)amino]acetyl]amino]methyl]-7-oxabicyclo[2.2.1]hept-2-yl]-5-heptenoic acid.

15. The method as defined in claim 1 wherein the thromboxane A₂ receptor antagonist has the name [1S-[1α,2β(5Z),3β,4α]]-7-[3-[[2-(phenylamino) carbonyl]-hydrazino]methyl]-7-oxabicyclo [2.2.1]hept-2-yl]-5-heptenoic acid.

16. The method as defined in claim 1 wherein the thromboxane A₂ receptor antagonist has the name 4-(3-((4-chlorophenyl)sulfonyl)propyl)benzene acetic acid.

17. The method as defined in claim 1 wherein the thromboxane A₂ receptor antagonist has the name or 4-[2-(benzenesulfamido)ethyl]phenoxyacetic acid or 4-[2-(4-chlorobenzenesulfonamido)-ethyl]phenylacetic acid.

18. The method as defined in claim 1 for reversing protamine/heparin induced pulmonary hypertension.

19. The method as defined in claim 1 for reducing protamine/heparin induced pulmonary hypertension.

20. A method for preventing pulmonary hypertension caused by protamine induced neutralization of heparin, in a mammalian species, which comprises administering to a mammalian species in need of such treatment an effective amount of a thromboxane A₂ receptor antagonist, said thromboxane A₂ receptor antagonist being administered before administering protamine, with protamine, with heparin or within several minutes after administering protamine, said thromboxane A₂ receptor antagonist acting only on thromboxane A₂ receptors.

* * * * *

UNITED STATES PATENT AND TRADEMARK OFFICE
CERTIFICATE OF CORRECTION

PATENT NO. : 5,066,480
DATED : Nov. 19, 1991
INVENTOR(S) : Martin L. Ogletree et al It is certified that error appears in the above-identified patent and that said Letters Patent is hereby corrected as shown below:

Column 7, line 2, delete "-" before 2.2.1] and insert --[--.

Column 7, claim 13, line 7, delete "-" before 2.2.1] and insert -- [ --.

Column 7, claim 14, line 11, insert < after "2" and before "β".

Column 8, line 7, delete hyphen before "ethyl]".

Signed and Sealed this

Twentieth Day of April, 1993

Attest:

MICHAEL K. KIRK

Attesting Officer    Acting Commissioner of Patents and Trademarks